United States Patent
Csutak

(10) Patent No.: US 9,249,656 B2
(45) Date of Patent: Feb. 2, 2016

(54) HIGH PRECISION LOCKED LASER OPERATING AT ELEVATED TEMPERATURES

(71) Applicant: Sebastian Csutak, Houston, TX (US)

(72) Inventor: Sebastian Csutak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 529 days.

(21) Appl. No.: 13/677,850

(22) Filed: Nov. 15, 2012

(65) Prior Publication Data

US 2014/0131034 A1 May 15, 2014

(51) Int. Cl.
| | |
|---|---|
| *E21B 47/00* | (2012.01) |
| *G01N 21/3504* | (2014.01) |
| *G01N 21/39* | (2006.01) |
| *H01S 5/0687* | (2006.01) |
| *E21B 47/10* | (2012.01) |

(52) U.S. Cl.
CPC .............. *E21B 47/00* (2013.01); *E21B 47/102* (2013.01); *G01N 21/3504* (2013.01); *G01N 21/39* (2013.01); *G01N 2021/399* (2013.01); *H01S 5/0687* (2013.01)

(58) Field of Classification Search
CPC ........ E21B 47/00–47/187; E21B 49/00–49/10
USPC ....................... 166/250.01–250.17
See application file for complete search history.

(56) References Cited

U.S. PATENT DOCUMENTS

| | | | |
|---|---|---|---|
| 4,050,033 A * | 9/1977 | Chang ..................... | H01S 3/223 359/342 |
| 5,327,105 A | 7/1994 | Liberman et al. | |
| 6,552,856 B1 | 4/2003 | Chen | |
| 6,611,341 B2 | 8/2003 | May | |
| 6,631,019 B1 | 10/2003 | Vujkovic-Cvijin et al. | |
| 6,693,928 B2 | 2/2004 | May | |
| 6,927,636 B2 | 8/2005 | Deng et al. | |
| 6,953,487 B2 | 10/2005 | Cliche et al. | |
| 7,520,158 B2 * | 4/2009 | DiFoggio ..................... | 73/19.1 |
| 7,638,761 B2 | 12/2009 | Csutak | |
| 7,825,736 B2 | 11/2010 | McGuyer et al. | |
| 8,050,301 B2 | 11/2011 | Wells et al. | |
| 8,448,495 B2 * | 5/2013 | Breviere et al. ............. | 73/31.05 |

(Continued)

FOREIGN PATENT DOCUMENTS

| | | |
|---|---|---|
| WO | 2010068870 A2 | 6/2010 |
| WO | 2012094007 A2 | 7/2012 |

OTHER PUBLICATIONS

PCT International Search Report and Written Opinion; International Application No. PCT/US2013/069079; International Filing Date: Nov. 8, 2013; Date of Mailing: Feb. 17, 2014; pp. 1-10.

(Continued)

*Primary Examiner* — Blake Michener

(74) *Attorney, Agent, or Firm* — Cantor Colburn LLP

(57) ABSTRACT

A system, method and apparatus for operating a laser at a downhole location is disclosed. A gas is configured to receive an output of a laser and to absorb a selected wavelength of the laser corresponding to a selected spectral line of the gas. A pressure device reduces broadening of the selected spectral line related to a temperature at the downhole location. A photodetector receives light from the gas chamber and provides a measurement related to the received light. A processor alters an operating parameter of the laser using the obtained measurement to operate the laser.

16 Claims, 7 Drawing Sheets

(56) References Cited

U.S. PATENT DOCUMENTS

| | | | |
|---|---|---|---|
| 2003/0134426 A1* | 7/2003 | Jiang et al. | 436/121 |
| 2003/0160164 A1* | 8/2003 | Jones | G01N 21/31 250/269.1 |
| 2004/0045705 A1* | 3/2004 | Gardner et al. | 166/250.01 |
| 2004/0065439 A1* | 4/2004 | Tubel et al. | 166/250.15 |
| 2004/0244970 A1* | 12/2004 | Smith, Jr. | 166/250.01 |
| 2004/0244971 A1* | 12/2004 | Shammai et al. | 166/250.1 |
| 2005/0007583 A1* | 1/2005 | DiFoggio | 356/301 |
| 2005/0111498 A1 | 5/2005 | Daiber et al. | |
| 2005/0117155 A1* | 6/2005 | Kosterev | 356/432 |
| 2006/0102343 A1* | 5/2006 | Skinner et al. | 166/250.1 |
| 2006/0266109 A1* | 11/2006 | DiFoggio | 73/152.55 |
| 2007/0013911 A1 | 1/2007 | DiFoggio | |
| 2007/0068242 A1 | 3/2007 | DiFoggio | |
| 2007/0081157 A1* | 4/2007 | Csutak et al. | 356/301 |
| 2007/0272406 A1* | 11/2007 | McCoy et al. | 166/250.01 |
| 2009/0038794 A1* | 2/2009 | Yamate et al. | 166/254.2 |
| 2009/0114013 A1* | 5/2009 | DiFoggio | 73/382 R |
| 2010/0263862 A1* | 10/2010 | Goodwin | 166/252.5 |
| 2012/0273269 A1 | 11/2012 | Rinzler et al. | |
| 2012/0312530 A1* | 12/2012 | Pope et al. | 166/250.01 |
| 2013/0062514 A1* | 3/2013 | Csutak | 250/262 |
| 2014/0346157 A1* | 11/2014 | Bozso et al. | 219/121.85 |

OTHER PUBLICATIONS

Gilbert, Sarah L. et al.; Hydrogen Cyanide H13C14N Absorption Reference for 1530 nm to 1565 nm Wavelength Calibration—SRM 2519a, NIST Special Publication 260-137, 2005 Edition, pp. 1-10, Appendix A and B.

Vanier, Jacques et al.; "On the Use of Intensity Optical Pumping and Coherent Population Trapping Techniques in the Implementation of Atomic Frequency Standards," IEEE Transaction on Instrumentation and Measurements, vol. 52, No. 3, Jun. 2003, pp. 823-831.

\* cited by examiner

HIGH PRECISION LOCKED LASER OPERATING AT ELEVATED TEMPERATURES

BACKGROUND OF THE DISCLOSURE

1. Field of the Disclosure

The present disclosure is related to performing an operation in a wellbore and, in particular, to operation of a laser at a downhole location.

2. Description of the Related Art

In various drilling operations, it is useful to dispose a laser at a downhole location in order to perform a measurement or a downhole operation. Often, the accuracy of a laser-based downhole measurement is dependent on the wavelength of the laser. However, the wavelength of the laser may drift with temperature and/or other downhole conditions. In order to maintain a laser operating at a selected frequency at a downhole location, it is necessary to lock the laser at a selected wavelength. One method of locking a laser includes the use of a Fabry-Perot etalon. The etalon needs to have a low coefficient of expansion and be transparent at laser wavelengths. Zerodur® is a material that meets these requirements but has bad temperature stability at downhole temperatures. However, in a downhole environment, the temperature can range between about 120° C. and 200° C. and the temperature of the Zerodur® needs to be controlled within a few millidegrees in order to achieve high locking precision. Additionally, downhole operations require that this etalon control be maintained for up to 12 hours or longer. Another method of laser locking uses a spectral line of a gas to provide a wavelength standard. This method can also be affected by downhole temperatures and other conditions encountered downhole. Therefore, there is a need to provide a method and apparatus for maintain operation of a laser downhole at a selected wavelength.

SUMMARY OF THE DISCLOSURE

In one aspect, the present disclosure provides a method of operating a laser at a downhole location that includes: directing a laser beam from the laser onto a gas disposed at the downhole location; reducing a broadening of a selected spectral line of the gas related to a temperature at the downhole location; obtaining a measurement related to absorption of the laser at the selected spectral line; and altering an operating parameter of the laser using the obtained measurement to operate the laser.

In another aspect, the present disclosure provides an apparatus for operating a laser at a downhole location that includes: a gas configured to receive an output of the laser and to absorb a selected wavelength of the laser corresponding to a selected spectral line of the gas; a pressure device configured to reduce broadening of the selected spectral line related to a temperature at the downhole location; a photodetector configured to receive light from the gas chamber and provide a measurement related to the received light; and a processor configured to alter an operating parameter of the laser using the obtained measurement to operate the laser.

In another aspect, the present disclosure provides a system for performing an downhole operation including: a drill string; a laser disposed on the drill string at a downhole location; a gas configured to receive an output of the laser and to absorb a selected wavelength of the laser corresponding to a selected spectral line of the gas; a pressure device configured to reduce broadening of the selected spectral line related to a temperature at the downhole location; a photodetector configured to receive light from the gas chamber and provide a measurement related to the received light; and a processor configured to alter an operating parameter of the drill string to perform the downhole operation.

Examples of certain features of the apparatus and method disclosed herein are summarized rather broadly in order that the detailed description thereof that follows may be better understood. There are, of course, additional features of the apparatus and method disclosed hereinafter that will form the subject of the claims.

BRIEF DESCRIPTION OF THE DRAWINGS

For detailed understanding of the present disclosure, references should be made to the following detailed description, taken in conjunction with the accompanying drawings, in which like elements have been given like numerals and wherein.

DETAILED DESCRIPTION OF THE DISCLOSURE

Figure 1:
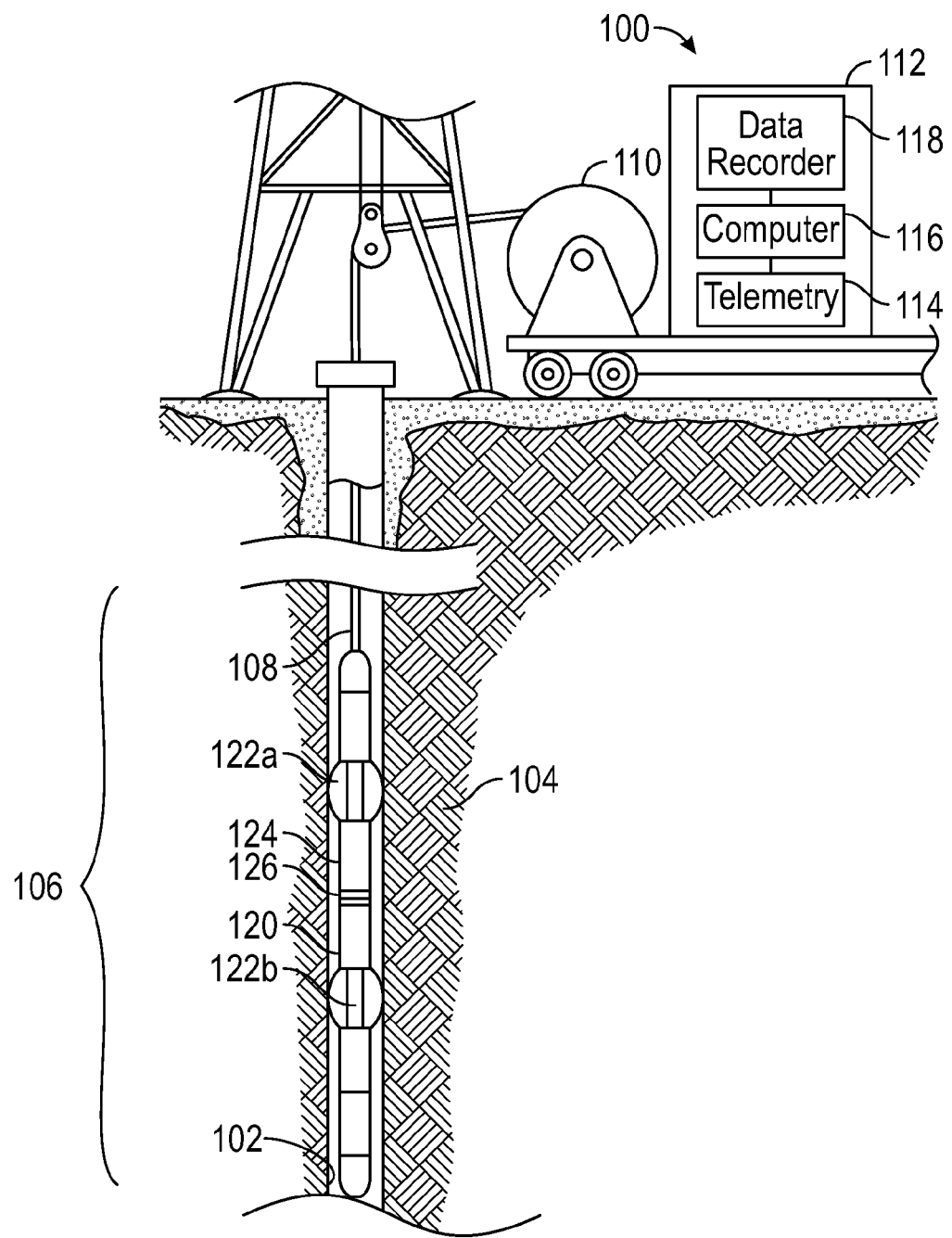
FIG. 1 shows an exemplary well logging apparatus according to an exemplary embodiment of the disclosure.

FIG. 1 shows an exemplary well logging apparatus 100 according to an exemplary embodiment of the disclosure. The well logging apparatus 100 is shown disposed in a well borehole 102 penetrating an earth formation 104 for making measurements of properties of the earth formations 104. The borehole 102 may be filled with drilling fluid to prevent formation fluid influx. The well logging apparatus 100 may include a logging tool string 106 lowered into the well borehole 102 by an electrical cable 108. The tool string 106 may be centered within the well borehole 102 by a top centralizer 122a and a bottom centralizer 122b attached to the logging tool string 106 at axially spaced apart locations. The centralizers 122a, 122b may be of types known in the art such as bowsprings. The cable 108 may be spooled and unspooled from a winch or drum 110 to raise and lower the logging tool string 100. The logging tool string 106 may include one or more logging devices 120 that may be electrically connected to surface equipment 112 by an optical fiber forming part of the cable 108. The surface equipment 112 may include one part of a telemetry system 114 for communicating control signals and data to the tool string 106 and computer 116. The computer 116 may also include a data recorder 118 for recording measurements made by the apparatus and transmitted to the surface equipment 112.

Circuitry for operating the one or more logging devices 120 may be located within an electronics cartridge 124 of the logging tool string 106. The circuitry may further be connected to the one or more logging devices 120 through a connector 126. In several embodiments, the one or more logging devices 120 may incorporate a laser for use in various downhole operations and/or downhole measurements as well as a device for maintaining operation of the laser at a selected frequency in the downhole environment.

Figure 2:
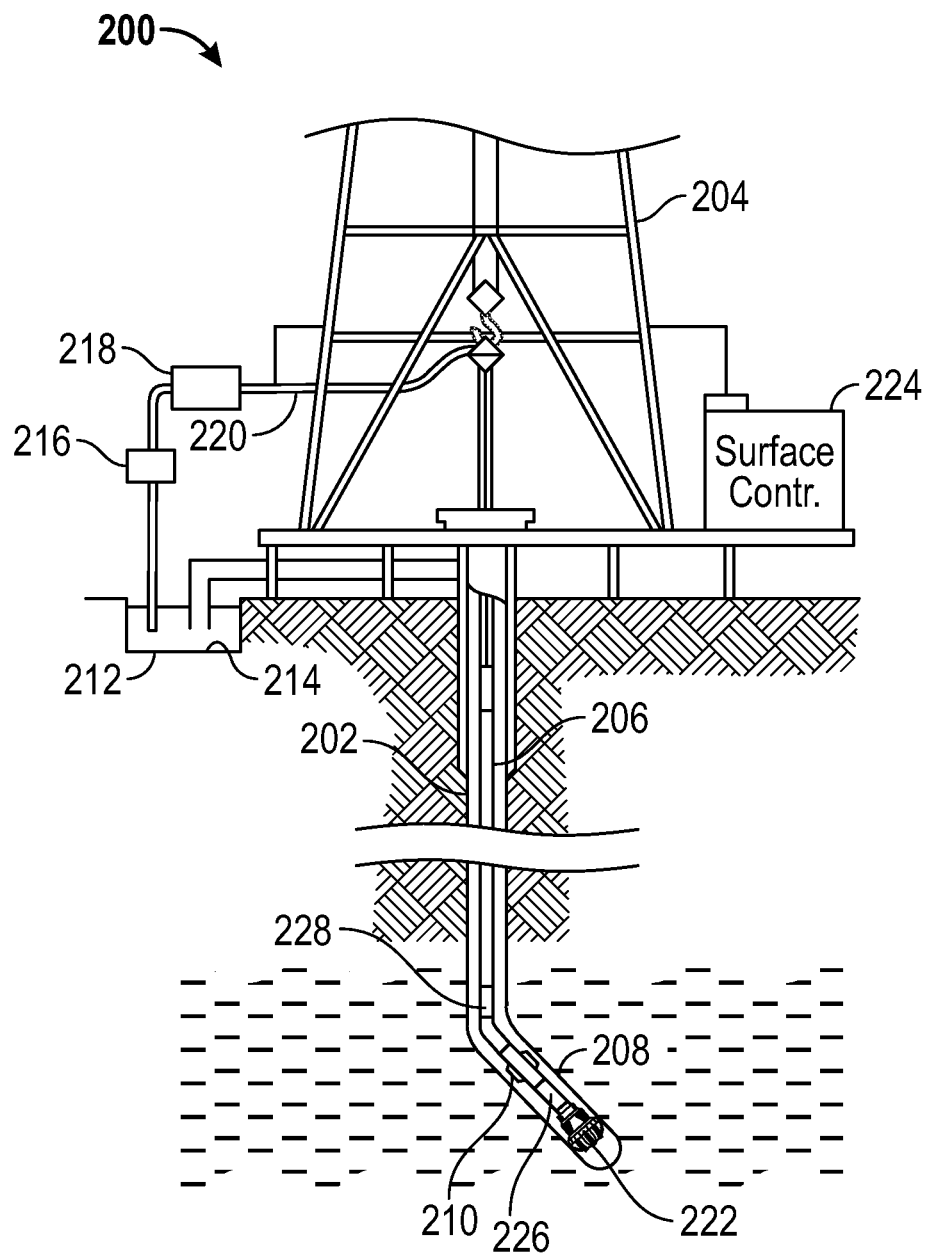
FIG. 2 is an elevation view of a measurement-while-drilling (MWD) system that may incorporate various embodiments of the disclosure.

FIG. 2 is an elevation view of a measurement-while-drilling (MWD) system 200 that may incorporate various embodiments of the disclosure. A well borehole 202 is drilled into the earth under control of surface equipment including a drilling rig 204. In accordance with a conventional arrangement, drilling rig 204 includes a drill string 206. The drill string 206 may be a coiled tube, jointed pipes or wired pipes as understood by those skilled in the art. The drill string 206 may include a bottom hole assembly (BHA) 208 having one or more logging devices 210 disposed thereon. The drill string 206 may further include a downhole drill motor 226 for rotating a drill bit 222 disposed at a bottom end of the drill string 206.

The exemplary MWD system 200 may include a drilling fluid 212 circulated from a mud pit 214 through a mud pump 216, past a desurger 218, through a mud supply line 220. The drilling fluid 212 may flow down through a longitudinal central bore in the drill string 206, and through jets (not shown) in the lower face of the drill bit 222. Return fluid containing drilling mud, cuttings and formation fluid flows back up through an annular space between the outer surface of the drill string 206 and the inner surface of the borehole 202 to be circulated to the surface where it is returned to the mud pit 214.

The exemplary MWD system 200 may include a surface controller 224 for processing commands and other information used in the drilling operations. The surface controller 224 may include a processor, memory for storing data, data recorder and other peripherals. The surface controller 224 may also respond to user commands entered through a suitable device, such as a keyboard.

In one embodiment, the BHA 226 contains various sensors and logging-while-drilling (LWD) devices incorporating aspects of the disclosure to provide information about the formation, downhole drilling parameters and the mud motor. In several embodiments, the logging devices 210 may incorporate a laser for performing downhole operations and/or downhole measurements and a device for maintaining operation of the high-gain semiconductor laser at a selected frequency in the downhole environment, as disclosed herein.

The MWD system 200 may use any conventional telemetry methods and devices for communication between the downhole components and the surface, such as the surface In an exemplary embodiment, mud pulse telemetry techniques are used to communicate data from downhole to the surface during drilling operations. A telemetry system 228 may be located in a suitable location on the drill string 206 such as above the logging devices 210. The telemetry system 228 may be used to receive commands from, and send data to, the surface via the mud pulse telemetry described above or by other communication techniques known in the art. Acoustic pipe telemetry and/or wired pipe telemetry may be used, for example.

Figure 3:
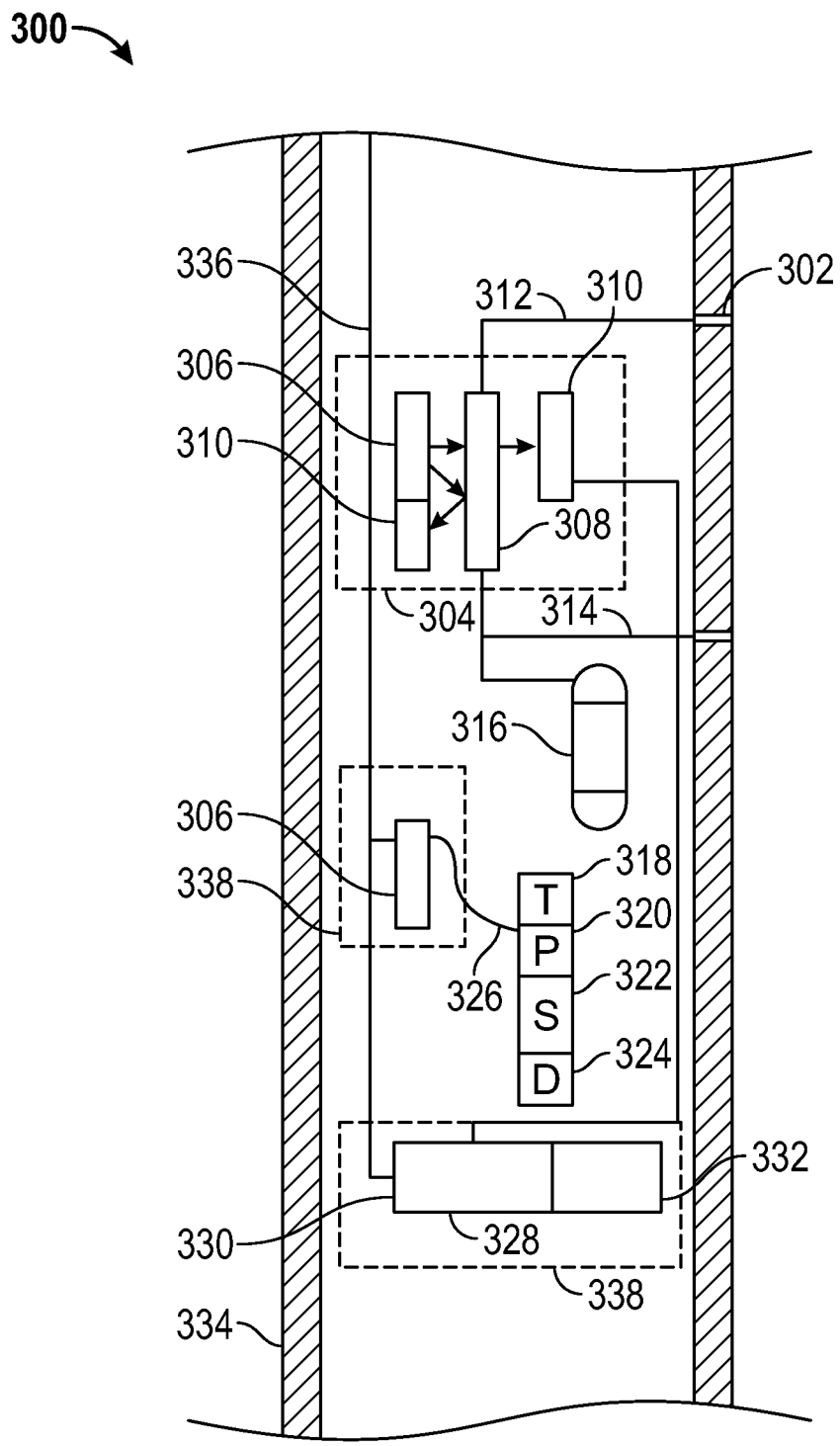
FIG. 3 shows an exemplary tool for conducting a downhole operation using the exemplary apparatus and methods disclosed herein.

FIG. 3 shows an exemplary tool 300 for conducting a downhole operation using the exemplary apparatus and methods disclosed herein. The exemplary tool 300 may be disposed to a downhole location via carrier 334 that carries the tool 300 into a well borehole. The carrier 334 may be configured for conveying the tool 100 either on a wireline apparatus such as shown in FIG. 1 or an MWD apparatus as shown in FIG. 2. In several examples, the carrier 334 may include a jointed pipe, a wired pipe, a coiled tube or a wireline. Some or all of these carrier examples may be combined. The tool 300 may include any number of devices for conducting downhole operations, and several devices may include a laser device 306 selected for operation in the high temperatures typical of the downhole environment. In one example, the tool 300 may include a spectrometer 304. In another example, the tool 300 may include one or more of a temperature sensor 318, a pressure sensor 320, a stress sensor 322 and/or a distance sensor 324. The stress sensor may also be acceleration and/or a vibration sensor. A downhole computing device 328 may include a processor 330 and a memory 332. The downhole computing device 328 may be coupled to the spectrometer 304 when included in the tool 300. In several examples, the downhole computing device 328 may be in communication with other sensors 318, 320, 322, 325, when included, and may further be in communication with a high-gain semiconductor 306 used with the several sensors. Power and data may be conveyed to and from the sensors, spectrometer and computing device using an electrical conductor cable 336. In some cases, an optical fiber 326 may be used for communicating information between tool components.

Several tool devices according to the disclosure may be used to sample and/or test formation or well bore fluids. A port 302 may be used to convey fluid into the tool 300 through a fluid conduit 312. In some cases, a sample chamber 316 may be included for holding or transporting fluid samples. Fluids may be expelled from the tool when desired by including a port 314 for directing the fluids into the annulus out side of the tool 300.

The exemplary spectrometer 304 may include a laser device 306, a sample region 308 and one or more detectors 310. In several embodiments, the laser device 306 may include a high-gain semiconductor used as a laser light source. The laser device 306 may provide light having a broader emission band than that of a laser where such a light source is desired. In an exemplary embodiment, the laser device 306 may be selected for high-temperature operation. The several sensors 318, 320, 322, and 324 described above may also include a laser device 306 emitting laser or other useful light. In some cases, sensors or other tool devices may use a high-gain semiconductor device such as a FET, LED, MOSFET, transistor, diode or the like where the semiconductor includes the high-temperature structure.

The spectrometer 304 may be used for measuring refractive index of the formation fluid. In this case, the light detector 310 may be located so as to receive light after reflection and refraction from a fluid sample in the fluid sample region 308. In other examples, the detector 310 may be placed such that light emitted from the laser device 306 passes through the sample region 308 and is detected at the detector 310.

Alternatively, the laser device 306 may supply a laser beam fro use in an interferometer or a gravimeter. The gravimeter may employ an interferometer as well. The precision of the wavelength of the laser beam allows for precise determination of interference fringe measurements. In an exemplary embodiment of the present disclosure, the precision may be carried out 10 decimal places.

While the laser device 306 of the present disclosure may be used at downhole temperatures without cooling, it is contemplated that temperature control devices 338 may be utilized for controlling a temperature of the laser devices 306. Examples of temperature control devices 338 may include sorption cooling devices, Dewar and thermo-electric cooling devices. While the high-gain semiconductor device 306 is shown with respect to spectrometer 304, it is to be understood that the laser device 306 may be used in any suitable apparatus or to perform any suitable operation that uses a laser having a wavelength maintained at a selected frequency, as disclosed herein.

Figure 4:
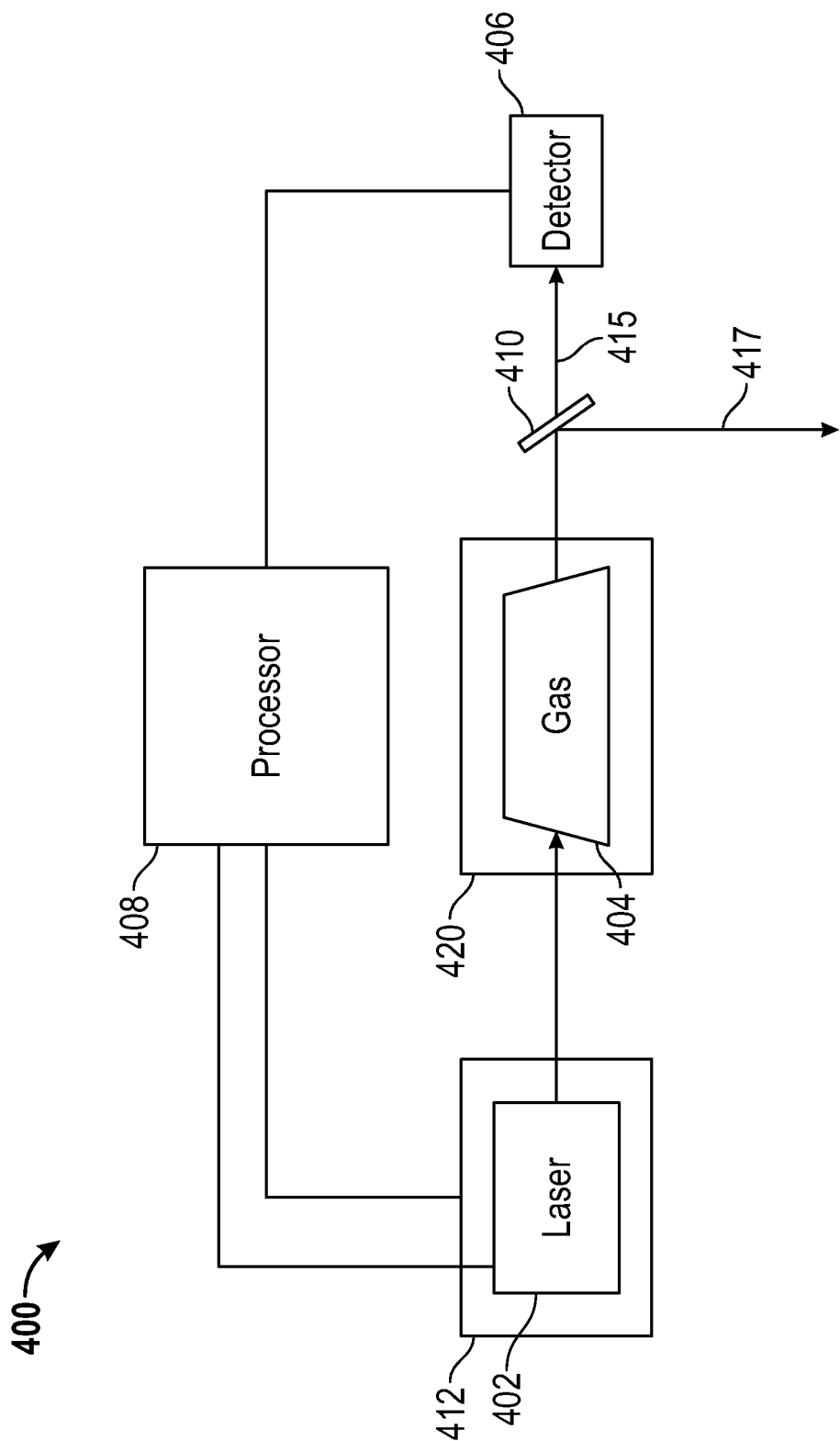
FIG. 4 shows a schematic view of an exemplary laser device in one embodiment of the present disclosure.
Figure 5:
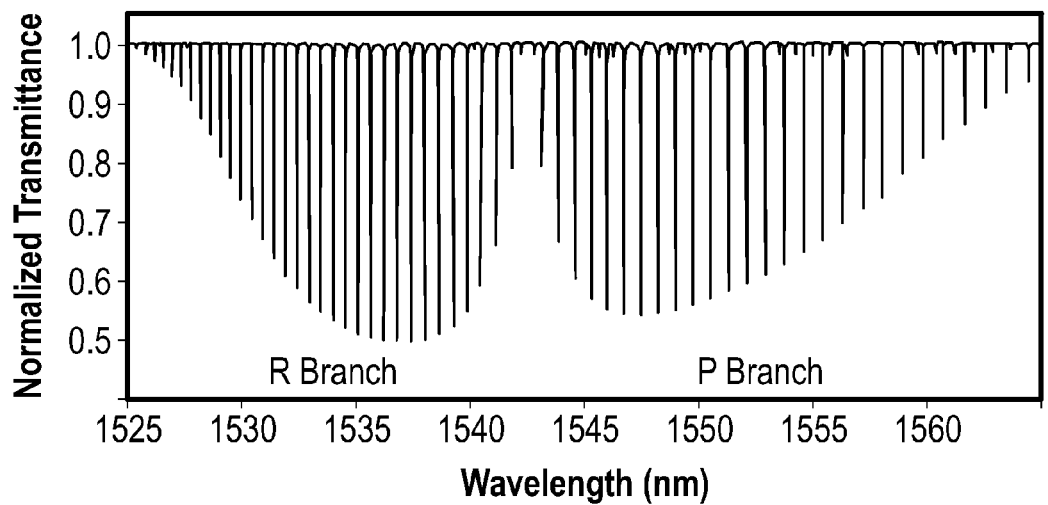
FIG. 5 (Prior Art) shows an exemplary rotational-vibrational absorption spectrum for $H_{13}C_{14}N$.

FIG. 4 shows a schematic view 400 of an exemplary laser device 306 in one embodiment of the present disclosure. The exemplary laser device 306 includes a laser 402, a gas chamber 404 containing a gas, and a detector 406. The laser 402 may be, for example, a tunable laser, such as a diode laser, a fiber laser, a quantum dot-based semiconductor diode laser, etc. In an exemplary embodiment, the operating wavelength of the laser may be affected by a temperature of the laser, an operating current of the laser and other parameters. The laser may drift up to about 50 kilohertz per degree Celsius. The laser 402 may be disposed in a temperature control device 412 that may be used to control an operating temperature of the laser, thereby controlling an operating wavelength of the laser. The gas chamber 404 may contain a gas having absorption spectral lines at selected wavelengths. In an exemplary embodiment, the spectral lines may be due to molecular rotational and vibrational modes of the gas. An exemplary gas may include $H_{13}C_{14}N$, which exhibits rotational and vibrational spectral lines in a spectral range from about 1530 nanometers (nm) to about 1565 nm. FIG. 5 shows an exemplary rotational-vibrational absorption spectrum for $H_{13}C_{14}N$. Other gases having rotational-vibrational spectral lines may also be used. A beam splitter 410 splits a laser beam exiting the gas chamber 404 into a first beam 415 and a second beam 417. The first beam 415 is directed to a detector 406 for detection and the second beam 417 is directed to an external device (not shown) for use in performing a downhole operation or obtaining a downhole measurement, for example. Detector 406 may be a photodetector that produces a current in response to light being captured at the photodetector. In an exemplary embodiment, a magnitude of the current at the photodetector 406 is related to an intensity of light in the first beam 415. The intensity of light in the first beam 415 may be related to a difference between a wavelength of the laser and a wavelength of an absorption line (spectral line) of the gas in the gas chamber 404. As the laser wavelength changes with respect to a selected spectral line of the gas, the intensity of light at the photodetector 406 changes. Thus, the current measurement at the photodetector 406 reflects this change in wavelength. Pressure chamber 420 may be used to alter a pressure of the gas at the downhole location to reduce broadening effects on the spectral lines of the gas due to downhole temperatures, thereby increasing a precision of the laser control system.

A processor 408 is coupled to the photodetector 406 and to the laser 402. The processor may receive a current measurement from the photodetector 406 and use the current measurement to determine a wavelength of the laser. Additionally, the processor 408 may control an operational parameter of the laser 402 to correct for a wavelength drift of the laser 402 from a selected spectral line of the gas. The processor 408 may control a temperature of the laser 402 and/or an operating current of the laser 402, among other operational parameters, in various embodiments, to control the wavelength of the laser 402.

Figure 6:
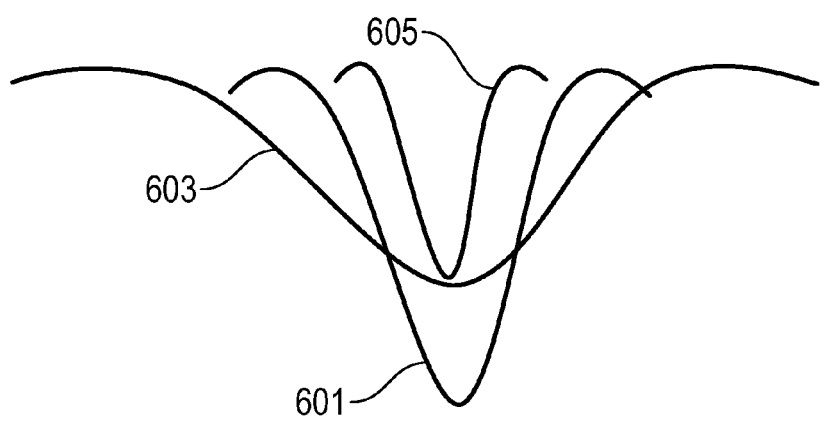
FIG. 6 shows exemplary spectral lines of the gas in a gas chamber under various conditions.

FIG. 6 shows exemplary a selected spectral line of the exemplary gas under various conditions. Spectral line 601 represents a spectral line of the exemplary gas at approximately room temperature. Broadened spectral line 603 represents a spectral line of a gas at an elevated temperature such as encountered at a downhole location. As the temperature of the gas increases, the thermal velocities of the gas molecules increase, thereby broadening spectral line 601 and reducing the peak at the central wavelength to obtain broadened spectral line 603. Thus, spectral line 603 has a broader line width and the absorption at the central wavelength of the spectral line 603 line is less than then absorption of the central wavelength of spectral line 601. Spectral line 605 correspond to pressure-reduces gas in a downhole location. Pressure of the gas plays a dominant role in the spectral broadening. Reducing the pressure of the gas reduces spectral broadening of line 603 to obtain spectral line 605. Therefore, in one embodiment, the pressure chamber 420 may be used to reduce a pressure of the gas in the gas chamber 404. The central wavelength is the same for the spectral lines 601, 603 and 605. However, since the peak of spectral line 605 is less than the peak of spectral line 601, spectral line 605 absorbs less light that spectral line 601 at the central wavelength. In order to provide additional absorption at the selected wavelength, the laser beam may be made to pass through more gas than it would for a gas at room temperature at a surface location. Thus, the gas chamber 404 may be longer than a gas chamber used at a room temperature to increase the path of the laser through the gas.

Figure 7:
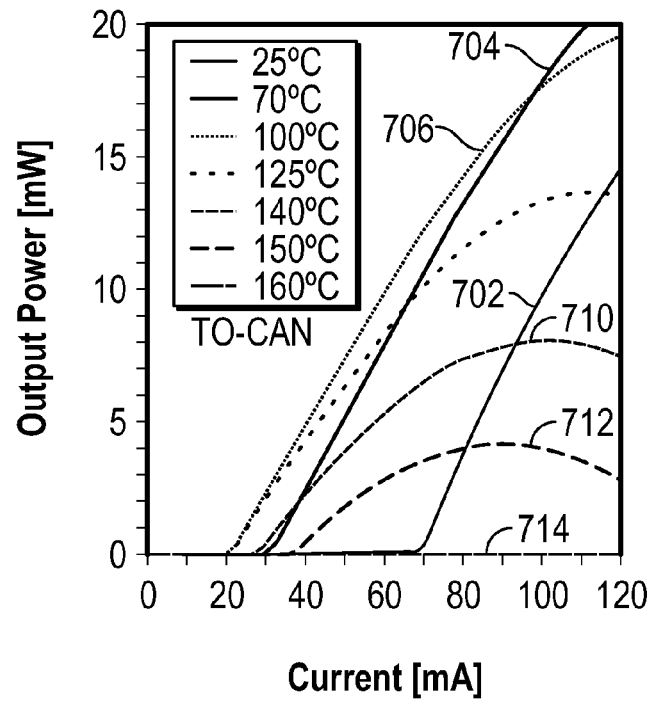
FIG. 7 shows a relation between laser output power and an operating current of an exemplary laser of the present disclosure.

FIG. 7 shows a relation between laser output power (optical power) and an operating current of an exemplary laser of the present disclosure. Power-current curves are displayed for several operating temperatures. Curve 702 shows a power-current curve at about 25° C. or at about room temperature. There is substantially no optical power output for currents below a cutoff current of about 70 milliamps (mA). However, above about 70 mA, the optical power increases with operating current in a substantially linear fashion. In an exemplary embodiment, the laser is operated in a range over which there is an approximately linear relation between power and current. Thus, at room temperatures, a suitable operational range of the laser is above about 70 mA. As the temperature increases to 70° C. (curve 704) and 100° C. (curve 706), the cutoff current decreases. Increasing the temperature further to 125° C. (curve 708), 140° C. (curve 710) and 150° C. (curve 712), a peak appears in the relation between optical power and current. The power-current relation is generally non-linear at the peak. Therefore, the linear region of the power-current relation is reduced at these higher temperatures. For a temperature of 150° C. (curve 712), this approximately linear region is between about 35 mA and about 60 mA. This linear region corresponds to less than about 3 mW of optical power. As shown in FIG. 7, a temperature of 160° C. (curve 714) is approximately an operating limit of the laser, since no output power is provided at any operating currents. Therefore, in an exemplary embodiment, a temperature of the laser may be maintained at the about 150° C. (curve 712) at the downhole location.

Figure 8:
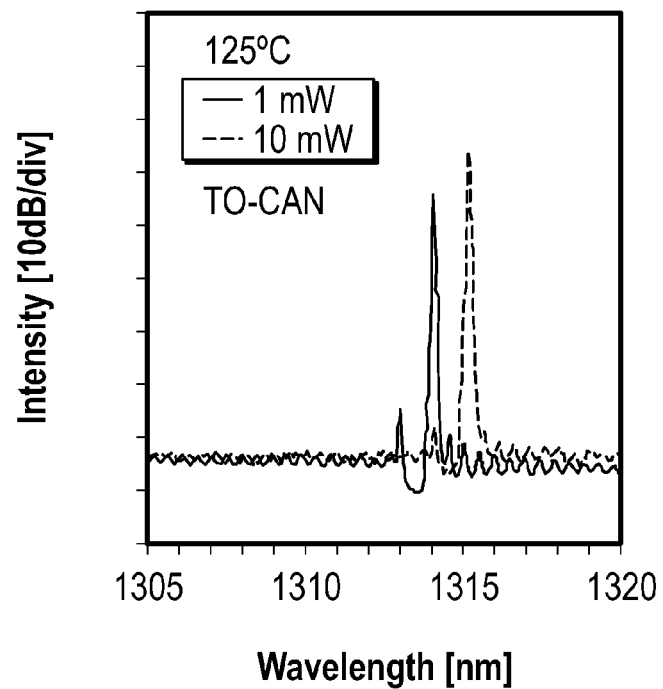
FIG. 8 shows exemplary wavelengths of a laser beam that may be emitted using the laser described in FIG. 7.
Figure 9:
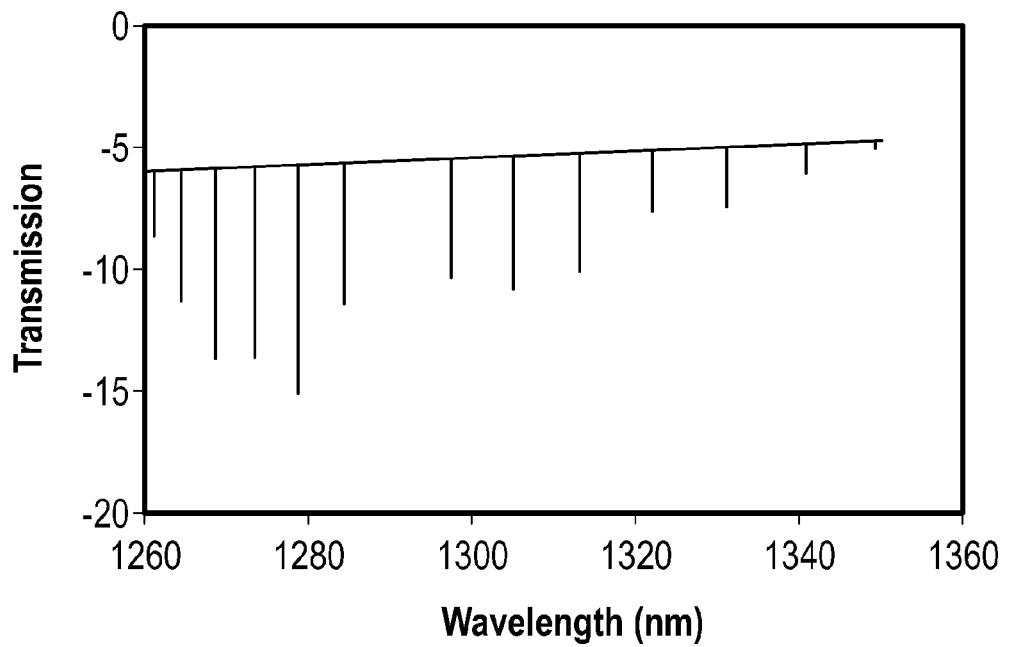
FIG. 9 shows a rotational-vibrational absorption spectrum for a hydrogen fluoride (HF) gas.

FIG. 8 shows exemplary wavelengths of a laser beam that may be emitted using the laser described in FIG. 7. The wavelengths are show for the laser operated at 125° C. The central wavelength of the laser is about 1314 nm at 1 milliwatt power and is about 1316 nm at 10 milliwatt power. As seen in FIG. 7, the laser is therefore capable of operating at this temperature to provide a substantial laser beam. Since the central wavelength is about 1314 nm to 1316 nm, the laser beam passed through a suitable gas that has spectral absorption lines at those comparable wavelengths. FIG. 9 shows a rotational-vibrational absorption spectrum for a hydrogen fluoride (HF) gas. The spectrum is in the same spectral region as the wavelength shown in FIG. 8 and may therefore be used in the gas chamber 404 for downhole laser locking of this laser beam.

Figure 10:
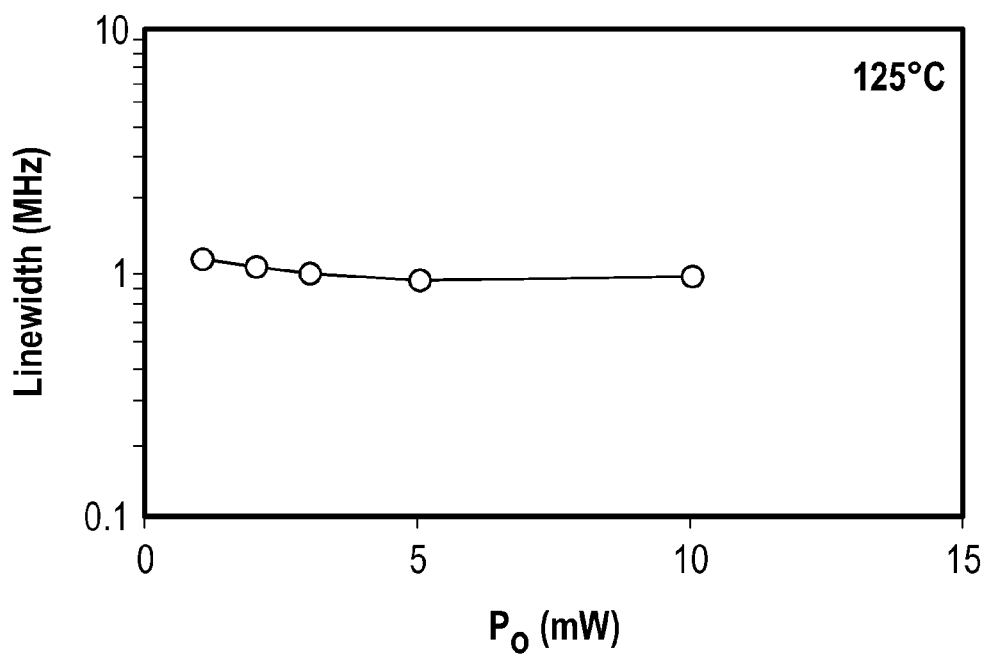
FIG. 10 shows a relation between laser line width and optical output power of the exemplary laser that may be achieved using the exemplary methods disclosed herein.

FIG. 10 shows a relation between laser line width and optical output power of the exemplary laser that may be achieved using the exemplary methods disclosed herein. The laser line width is shown for an operating temperature of about 125° C. The laser line width is about 1 megahertz (MHz) for optical output power between 1 mW and 10 mW. Therefore, the laser line width shows exceptional precision at these output powers.

In alternate embodiments, the locked laser beam may be used as part of a heterodyne laser in which at least one laser beam is locked to a selected wavelength. In other alternate embodiments, the laser may be locked to several absorption lines and measurements, such as interferometry measurements, may be made using the laser locked at each of the several absorption lines. Interpolation of the measurements may be the used to increase a precision of the measurements.

While the foregoing disclosure is directed to the certain exemplary embodiments of the disclosure, various modifications will be apparent to those skilled in the art. It is intended that all variations within the scope and spirit of the appended claims be embraced by the foregoing disclosure.

What is claimed is:

1. A method of operating a laser at a downhole location, comprising:
   directing a laser beam from the laser onto a gas disposed at the downhole location;
   reducing a broadening of a selected rotational-vibrational absorption line of the gas related to a temperature at the downhole location;
   obtaining a measurement related to absorption of the laser at the selected rotational-vibrational absorption line; and
   altering an operating parameter of the laser using the obtained measurement to operate the laser.

2. The method of claim 1, wherein reducing the broadening of the selected rotational-vibrational absorption line further comprises reducing a pressure of the gas at the downhole location.

3. The method of claim 1 further comprising operating a temperature of the laser at a temperature above the downhole temperature.

4. The method of claim 1, wherein obtaining the measurement relating to the absorption further comprises measuring a change in a photodiode current related to intensity of light from the gas that is captured by the photodiode.

5. The method of claim 1, wherein the operating parameter further comprises at least one of an operating current and an operating temperature of the laser.

6. The method of claim 1, wherein the operating parameter is an operating current and the operating current and the operating current is in a range over which optical power output of the laser is a substantially linear function of operating current.

7. The method of claim 1 further comprising altering the operating parameter of the laser to obtain a linewidth of the laser at about 1 megahertz (MHz).

8. An apparatus for operating a laser at a downhole location, comprising:
   a gas configured to receive an output of the laser and to absorb a selected wavelength of the laser corresponding to a selected rotational-vibrational absorption line of the gas;
   a pressure device configured to reduce broadening of the selected rotational-vibrational absorption line related to a temperature at the downhole location;
   a photodetector configured to receive light from the gas chamber and provide a measurement related to the received light; and
   a processor configured to alter an operating parameter of the laser using the obtained measurement to operate the laser.

9. The apparatus of claim 8, wherein the gas is disposed in a gas chamber and a length of the gas chamber is greater than a length of the gas chamber at a surface temperature to increase an absorption of the laser beam.

10. The apparatus of claim 8 further comprising a temperature control device configured to maintain a temperature of the laser at a temperature above the downhole temperature.

11. The apparatus of claim 8, wherein the measurement obtained at the photodiode further comprises a current measurement related to an intensity of light received at the photodiode from the gas.

12. The apparatus of claim 8, wherein the operating parameter further comprises at least one of an operating current and an operating temperature of the laser.

13. The apparatus of claim 12, wherein the processor is further configured to operate the laser at an operating current over which optical power output of the laser is substantially linearly related to the operating current.

14. The apparatus of claim 8, wherein the processor is further configured to alter the operating parameter of the laser to obtain a linewidth of about 1 megahertz (MHz).

15. A system for performing a downhole operation, comprising:
   a drill string;
   a laser disposed on the drill string at a downhole location;
   a gas configured to receive an output of the laser and to absorb a selected wavelength of the laser corresponding to a selected rotational-vibrational absorption line of the gas;
   a pressure device configured to reduce broadening of the selected rotational-vibrational absorption line related to a temperature at the downhole location;
   a photodetector configured to receive light from the gas chamber and provide a measurement related to the received light; and
   a processor configured to alter an operating parameter of the drill string to perform the downhole operation.

16. The system of claim 15, wherein the operating parameter of the drill string further comprises at least one of an operating current and an operating temperature of the laser.

* * * * *